United States Patent [19]

Mehlhorn et al.

[11] Patent Number: 5,070,091

[45] Date of Patent: * Dec. 3, 1991

[54] SUBSTITUTED 1,2,4-TRIAZINEDIONES USEFUL AGAINST PROTOZOA IN INSECTS

[75] Inventors: Heinz Mehlhorn, Neuss-Udesheim; Günter Schmahl, Bochum; Werner Lindner, Koeln; Axel Haberkorn, Wupperpal, all of Fed. Rep. of Germany

[73] Assignee: Bayer Aktiengesellschaft, Leverkusen, Fed. Rep. of Germany

[*] Notice: The portion of the term of this patent subsequent to Jun. 19, 2007 has been disclaimed.

[21] Appl. No.: 458,040

[22] Filed: Dec. 28, 1989

[30] Foreign Application Priority Data

Jan. 9, 1989 [DE] Fed. Rep. of Germany ....... 3900374

[51] Int. Cl.$^5$ .................. A01N 43/707; A01K 47/00
[52] U.S. Cl. ................................ 514/242; 424/407; 424/409; 424/411; 424/412; 424/413; 424/414; 424/410
[58] Field of Search .............. 424/405, 407, 409–413; 514/242

[56] References Cited

U.S. PATENT DOCUMENTS 4,837,216 6/1989 Mehlhorn et al. .................. 514/241
4,935,423 6/1990 Lindner et al. ..................... 514/242

*Primary Examiner*—Thurman K. Page
*Assistant Examiner*—Edward J. Webman
*Attorney, Agent, or Firm*—Sprung, Horn, Kramer & Woods

[57] ABSTRACT

Substituted 1,2,4-triazinediones of the formula

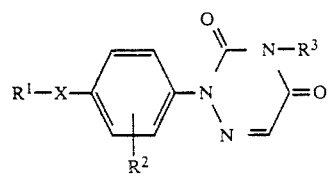

in which

R$^1$ represents an optionally substituted aromatic heteroaromatic radical which is bonded via carbon, X represents O, S, SO, SO$_2$ or

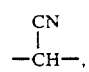

R$^2$ represents one or more identical or different radicals from the group comprising hydrogen, halogen, nitro, alkyl, alkoxy, halogenoalkyl and halogenalkoxy, R$^3$ represents hydrogen or optionally substituted alkyl, alkenyl, alkinyl or aralkyl, as well as their salts with bases. These compounds are useful for combating protozoa in insects.

7 Claims, No Drawings

SUBSTITUTED 1,2,4-TRIAZINEDIONES USEFUL AGAINST PROTOZOA IN INSECTS

The present invention relates to agents containing 1,2,4-triazinediones against parasitic Protozoa (unicellular organisms) in insects.

The Protozoa include parasites which are widespread in insects (for example *Nosema apis* in bees). They attack useful insects which are kept by man (for example bees or silk worms), but also those cultured in the laboratory and all insects living in the wild. The parasites damage the host animals by destroying their organs. Together with other parasites (for example Varroa mites in bees), they can cause considerable damage to the host animals which often leads to the death of the latter. In the case of the honey bee, they cause considerable damage by reducing honey production, and diminishing the colonies or causing them to die. When insects which are kept as a gene bank and for the preservation of species are cultured in laboratories, only a few animals are often present, and their death means that valuable information is lost.

It has been found that the substituted 1,2,4-triazinediones of the general formula (I)

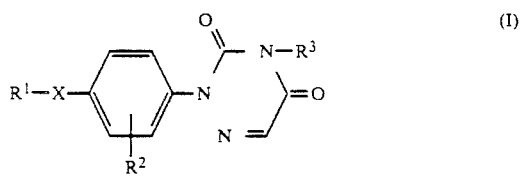

in which
R$^1$ represents optionally substituted aromatic radicals or optionally substituted heteroaromatic radicals which are bonded via carbon,
X represents O, S, SO, SO$_2$ or

R$^2$ represents one or more identical or different radicals from the group comprising hydrogen, halogen, nitro, alky,l, alkoxy, halogenoalkyl and halogenoalkoxy,
R$^3$ represents hydrogen or optionally substituted alkyl, alkenyl, alkinyl or aralkyl, as well as salts of these substituted 1,2,4-triazinediones with bases can be used for combating Protozoa in insects.

Some of the triazinediones are known from EP-OS (European Published Specification) 170,316, or they are the subject-matter of a previous, non-prior-published application assigned to the assignee of the present application.

Substituted 1,2,4-triazinediones of the general formula (I)

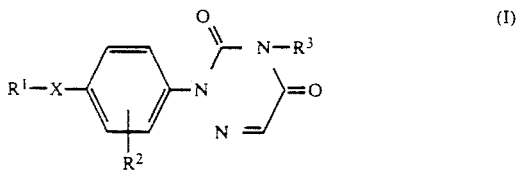

in which
R$^1$ represents optionally substituted heteroaromatic radicals which are bonded via carbon,
X represents O, S, SO or SO$_2$,
R$^2$ represents hydrogen or one or more identical or different radicals from the group comprising hydrogen, halogen, nitro, alkyl, alkoxy, halogenoalkyl and halogenoalkoxy,
R$^3$ represents hydrogen or optionally substituted alkyl, alkenyl, alkinyl or aralkyl,
can be prepared by
a) reacting compounds of the formula (II)

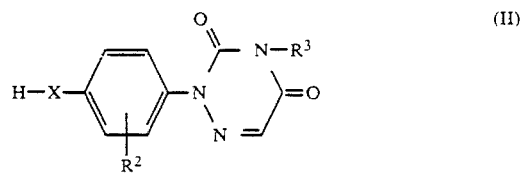

in which
X represents O or S,
R$^2$ and R$^3$ have the abovementioned meaning, with compounds of the formula (III)

in which
R$^1$ has the abovementioned meaning and
A represents the radicals halogen, O—SO$_2$-alkyl, —O—SO$_2$-halogenoalkyl, —O—SO$_2$-aryl or —S-alkyl,
or
b) for the preparation of compounds of the formula (I) in which R$^3$ does not represent hydrogen, reacting compounds of the formula (Ia)

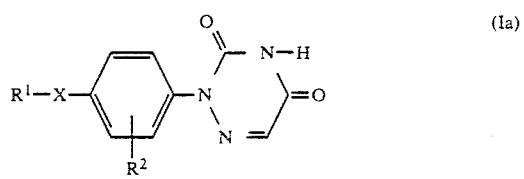

in which
R$^1$, R$^2$ and X have the abovementioned meaning, with compounds of the formula IV

in which
R$^3$ represents optionally substituted alkyl, alkenyl, alkinyl or aralkyl and
B represents halogen, —O—SO$_2$-alkyl, —O—SO$_2$-aryl or —O—SO$_2$-halogenoalkyl,
or
c) for the preparation of compounds of the formula I in which X represents —SO— or —SO$_2$—, reacting compounds of the formula I in which X represents S, with an oxidant.

The compounds of the formula (II)

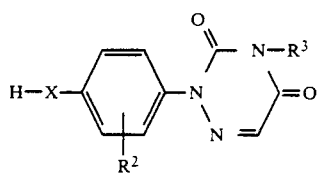
(II)

in which
X represents O or S,
R² represents one or more identical or different radicals on the group comprising halogen, nitro, alkyl, alkoxy, halogenoalkyl and halogenoalkoxy, and, in the event that X represents S, additionally represents hydrogen,
R³ represents hydrogen, alkyl, alkenyl, alkinyl or aralkyl, are new and are obtained by decarboxylating compounds of the formula (V)

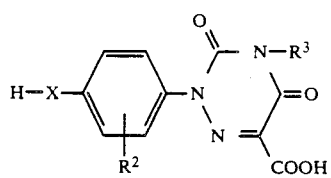
(V)

in which
X, R² and R³ have the abovementioned meaning, by heating.

The compounds of the formula (V)

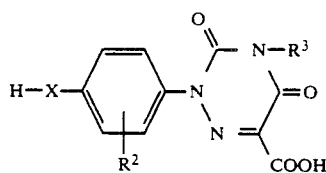
(V)

in which
X represents O or S,
R² represents one or more identical or different radicals from the group comprising halogen, nitro, alkyl, alkoxy, halogenoalkyl and halogenoalkoxy, and, in the event that X represents S, additionally represents hydrogen,
R³ represents hydrogen, alkyl, alkenyl, alkinyl or aralkyl, are new and are obtained by heating compounds of the formula (VI)

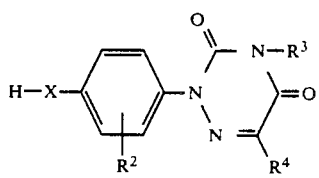
(VI)

in which
X, R² and R³ have the meaning given in (3),
R⁴ represents the radicals —CN and

R⁵ represents optionally substituted alkyl or aryl,
in the presence of aqueous acids.

The compounds of the formula (VI)

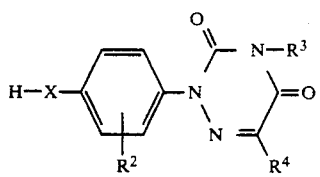
(VI)

in which
X, R², R³ and R⁴ have the abovementioned meaning, are novel and are obtained by heating compounds of the formula (VII)

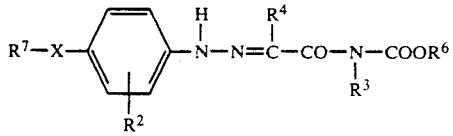
(VII)

in which
X, R², R³ and R⁴ have the abovementioned meaning and
R⁶ represents alkyl or optionally substituted aryl,
R⁷ represents hydrogen or optionally substituted

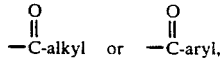

in the presence of bases.

The compounds of the formula (VII)

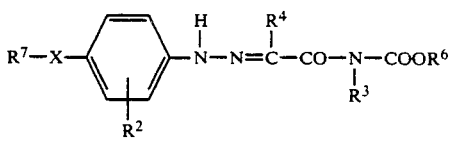
(VII)

in which
X, R², R³, R⁴, R⁶ and R⁷ have the abovementioned meaning and, in the event that R⁷ represents H or X represents S, R² can additionally represent hydrogen, are new and are obtained by initially diazotizing compounds of the formula (VIII)

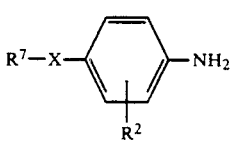
(VIII)

in which
X, R² and R³ have the abovementioned meaning,
in the presence of aqueous mineral acids, using alkali metal nitrite, and subsequently reacting the product with compounds of the formula (IX)

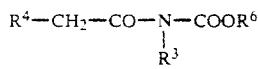  (IX)

in which

R³, R⁴ and R⁶ have the abovementioned meaning.

Compounds of the formula (I) which are preferably used are those in which $R^1$ represents phenyl, thiazolyl, oxazolyl, benzothiazolyl or benzoxazolyl, each of which is optionally substituted by halogen, alkyl, cyano, nitro, o-alkyl, s-alkyl or halogenoalkyl, X represents O, S or

$R^2$ represents halogen or $C_{1-6}$-alkyl, $R^3$ represents hydrogen or $C_1$-$C_4$-alkyl, in particular methyl.

Compounds of the formula (I) which are particularly preferably used are those in which X represents O or

$R^1$ represents thiazolyl, benzothiazolyl, benzoxazolyl or phenyl, each of which is optionally substituted by $C_{1-4}$-alkyl, in particular methyl, or $C_{1-4}$-halogenoalkyl, in particular trifluoromethyl, or halogen, in particular chlorine, bromine or fluorine, or nitro, or CN, or $C_{1-4}$-alkoxy, in particular methoxy, or $C_{1-4}$-halogenoalkoxy, in particular trifluoromethoxy, or $C_{1-4}$-alkylthio, in particular methylthio, or $C_{1-4}$-halogenoalkylthio, in particular trifluoromethylthio, $R^2$ one or more radicals of the group comprising hydrogen or halogen, in particular chlorine, bromine or $C_{1-4}$-alkyl, in particular methyl, $R^3$ represents hydrogen.

Compounds of the formula (I) which are very particularly preferably used are those in which X represents O, $R^1$ represents thiazolyl or benzothiazolyl, each of which is optionally substituted by chlorine or methyl or trifluoromethyl, $R^2$ represents one or more radicals from the group comprising hydrogen, methyl or chlorine, $R^3$ represents hydrogen.

Other compounds of the formula (I) which are particularly preferably used are those in which X represents

$R^1$ represents phenyl which is optionally substituted by chlorine, methyl or trifluoromethyl, $R^2$ represents one or more identical or different radicals from the group comprising hydrogen, chlorine or methyl, $R^3$ represents hydrogen or methyl.

The following may be mentioned in particular:

2-chloro-α-(4-chlorophenyl)-4-(4,5-dihydro-3,5-dioxo-1,2,4-triazin-2(3H)-yl)-phenylacetonitrile and 2,6-dichloro-α-(4-chlorophenyl)-4-(4,5-dihydro-3,5-dioxo-1,2,4-triazin-2(3H)-yl)-phenylacetonitrile.

Mention may also be made of the following individual compounds:

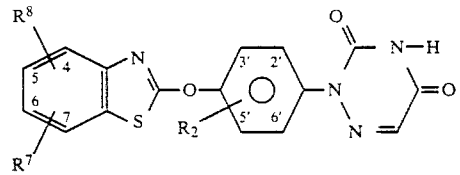

| R₂ | R⁷ | R⁸ |
|---|---|---|
| 3-CH₃ | 6-Cl | H |
| 3-CH₃ | 6-CF₃ | H |
| 3-CH₃ | 5-Cl | 6-Cl |
| 3,5-Cl | 6-Cl | H |
| 3,5-Cl | 6-CF₃ | H |
| 3,5-Cl | 5-Cl | 6-Cl |

Mention may furthermore be made of the following compounds:

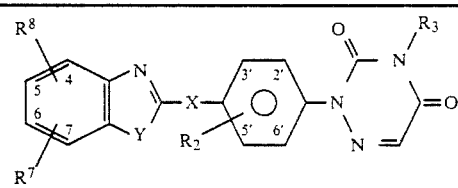

| Y | R₂ | X = O R₃ | R₇ | R₈ |
|---|---|---|---|---|
| S | H | H | H | H |
| S | H | H | 6-Cl | H |
| S | H | H | 6-Br | H |
| S | H | H | 6-F | H |
| S | H | H | 6-CH₃ | H |
| S | H | H | 6-OCH₃ | H |
| S | H | H | 6-NO₂ | H |
| S | H | H | 6-CN | H |
| S | H | H | 6-CF₃ | H |
| S | H | H | 6-SCF₃ | H |
| S | H | H | 6-OCF₃ | H |
| S | H | H | 5-Cl | 6-Cl |
| S | 3'-CH₃ | H | H | H |
| S | 3'-CH₃ | H | 6-Br | H |
| S | 3'-CH₃ | H | 6-F | H |
| S | 3'-CH₃ | H | 6-CH₃ | H |
| S | 3-CH₃ | H | 6-OCH₃ | H |
| S | 3-CH₃ | H | 6-NO₂ | H |
| S | 3-CH₃ | H | 6-CN | H |
| S | 3-CH₃ | H | 6-SCF₃ | H |
| S | 3-Cl | H | H | H |
| S | 3-Cl | H | 6-Cl | H |
| S | 3-Cl | H | 6-Br | H |
| S | 3-Cl | H | 6-F | H |
| S | 3'-Cl | H | 6-CH₃ | H |
| S | 3'-Cl | H | 6-OCH₃ | H |
| S | 3'-Cl | H | 6-NO₂ | H |
| S | 3'-Cl | H | 6-CN | H |
| S | 3'-Cl | H | 6-CF₃ | H |
| S | 3'-Cl | H | 6-SCF₃ | H |
| S | 3'-Cl | H | 6-OCF₃ | H |
| S | 3'-Cl | H | 5-Cl | 6-Cl |
| S | 3', 5'-Cl | H | H | H |
| S | 3', 5'-Cl | H | 6-Br | H |
| S | 3', 5'-Cl | H | 6-CH₃ | H |
| S | 3', 5'-Cl | H | 6-OCH₃ | H |
| S | 3', 5'-Cl | H | 6-NO₂ | H |
| S | 3', 5'-Cl | H | 6-CN | H |
| S | 3', 5'-Cl | H | 6-SCF₃ | H |
| S | 3', 5'-Cl | H | 6-OCF₃ | H |
| S | 3'-Cl, 5'-CH₃ | H | H | H |
| S | 3'-Cl, 5'-CH₃ | H | 6-Cl | H |

| | -continued | | | |
|---|---|---|---|---|
| S | 3'-Cl, 5'-CH$_3$ | H | 6-Br | H |
| S | 3'-Cl, 5'-CH$_3$ | H | 6-F | H |
| S | 3'-Cl, 5'-CH$_3$ | H | 6-OCH$_3$ | H |
| S | 3'-Cl, 5'-CH$_3$ | H | 6-CN | H |
| S | 3'-Cl, 5'-CH$_3$ | H | 6-CN | H |
| S | 3'-Cl, 5'-CH$_3$ | H | 6-CF$_3$ | H |
| S | 3'-Cl, 5'-CH$_3$ | H | 6-SCF$_3$ | H |
| S | 3'-Cl, 5'-CH$_3$ | H | 5-Cl | 6-Cl |
| S | 3'-CH$_3$, 5'-CH$_3$ | H | 6-Cl | H |
| S | 3'-CH$_3$, 5'-CH$_3$ | H | 5-Cl | 6-Cl |
| S | 3'-CH$_3$, 5-CH$_3$ | H | 5-Cl | H |
| S | 3'-Cl | H | 5-Cl | H |
| S | 3'-CH$_3$ | H | 5-Cl | H |
| S | 3'-Cl, 5'-CH$_3$ | H | 5-Cl | H |
| S | 3'-Cl, 5'-Cl | H | 5-Cl | H |
| S | 3'-Br | H | 6-Cl | H |
| S | 3'-Br, 5'-Br | H | 6-Cl | H |
| S | 3'-CF$_3$ | H | 6-Cl | H |
| S | 3'-CF$_3$, 5'-Cl | H | 6-Cl | H |
| O | 3'-Cl, 5'-Cl | H | 6-Cl | H |
| O | 3'-CH$_3$ | H | 6-Cl | H |
| O | 3'-CH$_3$ | H | 6-Cl | H |
| S | 3'-Cl, 5'-Cl | CH$_3$ | 6-CL | H |
| S | 3'-CH$_3$ | —C$_2$H$_5$ | 5-Cl | 6-Cl |

| Y | X | R$_2$ | R$_3$ | R$_7$ | R$_8$ |
|---|---|---|---|---|---|
| S | S | H | H | 6-Cl | H |
| S | S | H | H | H | H |
| O | S | H | H | H | H |
| O | SO | H | H | H | H |
| O | SO$_2$ | H | H | H | H |
| O | S | 3,5-Cl$_2$ | H | 6-Cl | H |
| O | S | 3,5-Cl$_2$ | H | H | H |

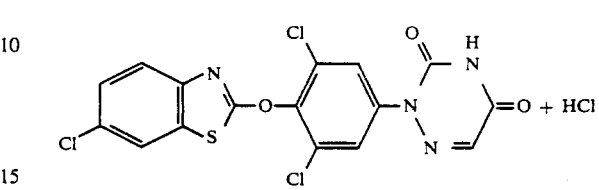

| Y | R$_2$ | R$_3$ | R$_7$ | R$_8$ |
|---|---|---|---|---|
| S | H | H | H | H |
| S | H | H | Cl | H |
| S | H | H | Cl | Cl |
| S | H | H | Cl | CF$_3$ |
| S | H | H | Cl | CH$_3$ |
| S | 3'-Cl | H | H | H |
| S | 3'-Cl | H | Cl | H |
| S | 3'-Cl | H | Cl | Cl |
| S | 3'-Cl | H | Cl | CF$_3$ |
| S | 3'-CH$_3$ | H | Cl | H |
| S | 3'-CH$_3$ | H | Cl | Cl |
| S | 3'-CH$_3$ | H | Cl | CF$_3$ |
| S | 3'-Cl, 5'-Cl | H | Cl | H |
| S | 3'-Cl, 5'-Cl | H | Cl | Cl |
| S | 3'-Cl, 5'-Cl | H | Cl | CF$_3$ |
| O | 3'-Cl, 5'-Cl | H | H | H |
| O | 3'-CH$_3$ | H | H | H |
| O | 3'-Cl, 5'-Cl | H | Cl | H |
| O | 3'-CH$_3$ | H | Cl | H |
| S | 3'-Cl, 5'-Cl | CH$_3$ | Cl | Cl |
| S | 3'-CH$_3$ | C$_2$H$_5$ | Cl | Cl |

If, in process 2, 2-(3,5-dichloro-4-hydroxyphenyl)-1,2,4-triazine-3,5(2H,4H)dione is employed as the compound II and 2,6-dichlorobenzothiazole as the compound of the formula III, the process may be described by the following equation

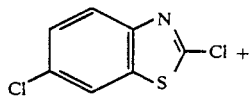

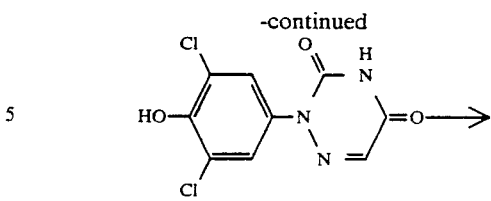

Compounds of the formula II in which R$^2$ and R$^3$ represent hydrogen, are known (J. Slouka, Acta Unio Palacki Olomuk. Fac. Rerum. Nat. 1984 (Chem 23), 39–45; C.A. 102 203946c).

Compounds of the formula II in which R$^2$ represents radicals other than hydrogen, are new.

Compounds of the formula II which may preferably be mentioned are those in which R$^2$ and R$^3$ have the preferred meanings mentioned in the case of the compounds of the formula I.

The following new compounds of the formula II may be mentioned individually.

| R$^2$ |
|---|
| 3-Cl |
| 3-CH$_3$ |
| 3,5-Cl$_2$ |
| 3,5-(CH$_3$)$_2$ |

The substituted heterocycles of the formula III are known or may be prepared analogously to known processes (Beilstein vol. 27; Katrizky and Rees, Comprehensive Het. Chem. Col. 6 1984).

They have the preferred meanings indicated hereinbefore in the case of the compounds of the formula I. The following compounds of the formula III may be mentioned individually.

| Y | R$^8$ | A |
|---|---|---|
| S | 6-Cl | Cl |
| S | 5,6-Cl | Cl |
| O | 6-Cl | Cl |
| O | 5,6-Cl | Cl |

| Y | R$^7$ | A |
|---|---|---|

-continued

| S | 4-Cl | Cl |
| S | 4,5-Cl | Cl |
| O | 4-Cl | Cl |
| O | 4,5-Cl | Cl |

The reaction is preferably carried out using diluents.

Diluents which are suitable for this purpose are virtually all inert organic solvents. These preferably include aliphatic and aromatic, optionally halogenated hydrocarbons, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethylphosphoric triamide.

The reaction is carried out in the presence of inorganic or organic acid acceptors.

Examples which may be mentioned are:

alkali metal hydroxides, such as, for example, sodium hydroxide and potassium hydroxide, alkaline earth metal hydroxides, such as, for example, calcium hydroxide, alkali metal carbonates and alkali metal alkoxides, such as sodium carbonate, potassium carbonate, sodium methoxide, potassium methoxide, sodium ethoxide and potassium ethoxide, furthermore aliphatic, aromatic or heterocyclic amines, for example triethylamine, pyridine, 1,5-diazabicylo-[4,3,0]-non-5-ene (DBN), 1,8-diazabicyclo-[5,4,0]-undec-7-ene (DBU) and 1,4-diazabicyclo-[2,2,2]-octane (DABCO).

The reaction is carried out at temperatures between 50° and 200° C., preferably between 80° and 160° C., under atmospheric pressure or elevated pressure. The reaction is preferably carried out under atmospheric pressure.

The process is carried out by combining equimolar amounts of the compounds of the formula II and III in one of the indicated diluents, and heating the mixture. When the reaction is complete, the reaction mixture is acidified using dilute inorganic acid (for example hydrochloric acid), and the precipitate which forms is filtered off, washed and dried.

If, in process 2b for the preparation of the compounds of the formula I in which $R^3$ does not represent hydrogen, 2-[4-[2'-benzothiazolyloxy]phenyl]1,2,4-triazine-3,5-(2H,4H)-dione is employed as the compound of the formula Ia and methyl iodide as the compound of the formula IV, the process may be described by the following diagram.

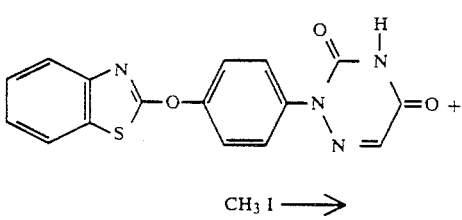

CH₃ I ⟶

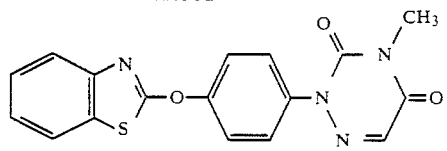

The compounds of the formula Ia are new and are prepared as described in process 2a.

The compounds of the formula IV are known or may be prepared by known methods. Methyl iodide and ethyl bromide may be mentioned in particular.

The process is carried out by reacting a compound of the formula Ia in the presence of a base and of a diluent with compounds of the formula IV. Diluents which can be employed are all inert organic solvents which also serve for carrying out process Ia.

The process is carried out in the presence of bases. Preferred bases which may be mentioned are the alkali metal hydroxides, such as sodium hydroxide, alkali metal alkoxides, such as sodium methoxide or potassium butoxide, metal hydrides, such as sodium hydride, or organic bases, such as 1,8-diazabicyclo[5,40]-undec-7-ene (DBU).

The process is carried out under atmospheric pressure and at temperatures between 20° and 140° C.

The reaction is carried out by combining equimolar amounts of the compound of the formula Ia and base, adding an equimolar amount of the compound of the formula IV to this mixture, and heating the mixture at the reaction temperature.

If, in process 2c) for the preparation of the compounds of the formula I where X=SO or SO₂,2-[4-[(2'benzoxazolylthio)phenyl]-1,2,4-triazine-3,5-(2H,4H)-dione is employed as the compound of the formula I, the process can be described by the following diagram.

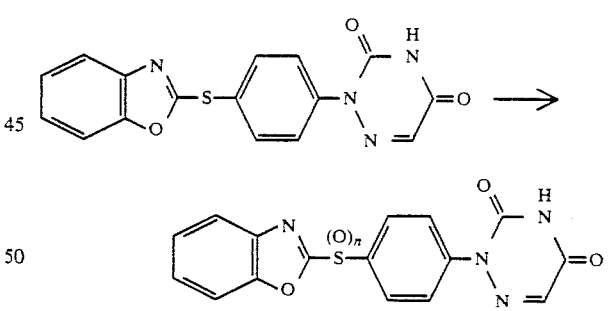

The process is carried out by treating a compound of the formula I where X=S with an oxidant in the presence of a diluent. The following oxidants are preferably used: hydrogen peroxide and other inorganic peroxides, such as sodium peroxide, organic peroxo acids, such as, for example, m-chloroperbenzoic acid and iodine-oxygen compounds, such as, for example, sodium metaperiodate.

The following can preferably be employed as diluents: alcohols, such as, for example, methanol, organic acids, such as, for example, acetic acid, and furthermore, ketones, such as acetone, halogenated hydrocarbons, such as dichloromethane, or acid anhydrides, such as acetic anhydride, can be used. The oxidation is carried out at temperatures between 0° C. and 120° C. The reaction is preferably carried out under atmospheric pressure.

The amount of oxidant can be varied between the single molar amount and the 10-fold molar amount. The reaction is carried out by stirring the compounds of the formula I where X=S together with one of the indicated oxidants in one of the abovementioned diluents for several hours at the reaction temperature indicated.

It was known that 1,2,4-triazinediones of the formula (I) in which

X represents

and

R¹ represents phenyl,
can be employed for combating Coccidia of mammals and of poultry. This action is also cited for the compounds of the formula (I) which were hitherto unknown. Nothing was known about the fact that the compounds of the formula (I) can be employed for combating Protozoa in insects.

The Protozoa which occur as insect parasites include the pests of the phylum Microsporidia, in particular of the genus Nosema. *Nosema apis*, the pathogen causing nosematosis in bees, may be mentioned in particular.

The insects include useful insects and cultured insects, which are kept by man, such as, for example, honey bees, silk worms, parasitical hymenopters, but also all insects which are kept in laboratory cultures and which are kept either for experimental purposes or as a gene bank.

The compounds of the formula (I) can be employed in all development stages of the insects.

Treatment can also be carried out with agents which contain, besides the active compounds indicated, active compounds against other pests. Thus, for example, in the case of bees, a combined treatment against *Nosema* and *Varroa jacobsoni* is possible when the agents contain, besides the active compounds indicated, for example synthetic phosphoric esters, such as coumaphos, malathion; formamidines, such as chlordimeform; phenothiazines, such as promazine; synthetic pyrethroids, such as flumethrin, cyfluthrin, cyhalothrin or amitraz or cymiazole.

The Protozoa on the insects can be treated in different ways:
1. by direct contact with the active compound. For this purpose, the latter is, for example, sprayed, dusted, fumigated, vaporized, misted or incorporated into carrier substances or applied onto the carrier substances which come in contact with the insects, and
2. by a systemic action, via the haemolymph of the insects. For this purpose, for example, the active compound is given together with the feed or drinking water, or, in the case of colony-forming insects, poured, sprayed or atomized into the hive.

In principle, the treatment can be carried out all year round.

Since Protozoa occur in greater numbers in the warm season, treatment at the beginning of the warm season is particularly preferred.

If the active compound is vaporized or misted, or if it is incorporated into carrier substances, the treatment is preferably carried out all year round.

In the case of honey bees, it is particularly advantageous to carry out the treatment at the time of winter feeding, or outside the breeding season.

In the case of honey bees, furthermore, the bee colony can also be treated as an artificial swarm. This can also be carried out during the breeding season.

Agents which are sprayed contain the active compound in concentrations of 0.1–50% by weight, preferably of 0.3–20% by weight.

Prior to use, the agents can be diluted to concentrations of active compound of $10^{-4}$–2% by weight, preferably $10^{-3}$–0.5% by weight. They are sprayed in a conventional manner, using customary equipment.

Either the insects, or their habitat or parts thereof, or their environment, are treated with these agents.

The agents contain the active compound in addition to diluents and/or emulsifiers which, in the concentrations applied, are tolerated by insects.

Suitable diluents are water, alcohols, such as methanol, ethyl alcohol, propanol, isopropyl alcohol, n-butyl alcohol, amyl alcohol and octanol;

glycols, such as propylene glycol, 1,3-butylene glycol, ethylene glycol and dipropylene glycol monomethyl ether; diethylene glycol monomethyl ether;

glycerol;

aromatic alcohols, such as benzyl alcohol;

carboxylic esters, such as, for example, ethyl acetate, benzyl benzoate, butyl acetate, propylene carbonate and ethyl lactate;

aliphatic hydrocarbons, oils, such as, for example, cottonseed oil, groundnut oil, maize germ oil, olive oil, castor oil and sesame seed oil;

ketones, such as, for example, acetone and methyl ethyl ketone;

synthetic monoglycerides and triglycerides with natural fatty acids.

Other compounds which are well suitable as diluents are compounds such as, inter alia, dimethyl sulphoxide, dimethylacetamide, dimethylformamide, N-methylpyrrolidone, dioxane and 2-dimethyl-4-oxymethyl-1,3-dioxolane.

Water as well as lower alcohols having up to 8 carbon atoms in the molecule, as well as lower ketones, such as methyl ethyl ketone, and ethers of ethylene glycol and propylene glycol, are particularly suitable.

It is possible to employ one or more diluents when the agents to be used according to the invention are prepared.

Suitable emulsifiers are:

anionic surfactants, such as Na lauryl sulphate, fatty alcohol ether sulphates, the monoethanolamine salts of mono/dialkyl polyglycol ether orthophosphoric esters or calcium alkylarylsulphonate, cationic surfactants, such as cetyltrimethylammonium chloride, ampholytic surfactants, such as di-sodium N-lauryl-β-iminodipropionate or lecithin, non-ionic surfactants, for example polyoxyethylated castor oil, polyoxyethylated sorbitan monooleate or sorbitan monostearate, glycerol monostearate, polyoxyethylene stearate or alkylphenol polyglycol ethers.

Preferred emulsifiers which may be mentioned are:

non-ionic, water-soluble emulsifiers having an HLB (hydrophilic/lipophilic balance value) greater than 10, for example Emulgator NP 10 ® (Bayer AG), alkylaryl polyglycol ether; Renex 678 ® (Atlas Chemical Industries), polyoxyethylene alkylaryl ether; Tween 40 ® (Atlas), polyoxyethylene sorbitan monopalmitate; Myri 53 ® (Atlas), polyoxyethylene stearate; Atlas G 3707 ®, polyoxyethylene lauryl ether; Atlas G 3920 ®, polyoxyethylene oleyl ether; Atlas G 9046 T ®, polyoxyethylene mannitan monolaurate; Emulgator 1371 B ® (Bayer AG), alkyl polyglycol ether; Emulgator 1736 ® (Bayer AG), alkyl polyglycol ether (oleyl polyglycol ether); Emulgator OX ® (Bayer AG), alkyl polyglycol ether (dodecyl polyglycol ether); Ninox BM-2 ® (Stepan Chemical Co.), ethoxylated nonylphenol; Triton X-100 ® (Rohm and Haas Co.), isooctylphenol polyethoxyethanol; Cremophor EL ®, polyoxyethylated castor oil.

The agents according to the invention contain the emulsifiers in concentrations of up to the 10-fold, preferably up to the 5-fold, amount of the active compound employed. In each case, the diluents are made up to the desired end concentration.

The agents are prepared by dissolving the active compound(s) in the solvent or in an emulsifier or emulsifier/solvent mixture, if required with heating. If necessary, the agents are diluted further to the desired concentration with water.

The dusting agents contain the active compound in addition to conventional carrier substances which are tolerated by insects and are suitable for the preparation of powders or wettable powders.

Suitable carrier substances are inorganic carrier substances, such as, for example, talc, kaolin, calcium carbonate, silicates, bentonites, furthermore organic carrier substances, such as, for example, starches, for example rice starch, sugar, cellulose and cellulose derivatives.

The agents are prepared by mixing the active compound(s) with the carrier substances, if appropriate with the addition of wetting agents. Examples of suitable wetting agents are the emulsifiers mentioned hereinbefore.

Agents which are fumigated contain the active compound in concentrations of $10^{-7}-2\%$ by weight per 100 g of carrier material. The carrier material used is the customary material for fumigating preparations.

Examples of agents for vaporizing the active compound are carrier materials which are impregnated with agents containing the active compound, or into which the active compound is incorporated. Paper, cardboard, cellulose, fabric, felt, fleece or leather discs or films, which are soaked with agents containing the active compound and which can be heated, for example by a heat source, are preferred. The electric or battery-charged vaporizing ovens which are customary for vaporizing discs may be mentioned as a heat source.

It is particularly advantageous to employ agents into which the active compound is incorporated or onto which it is applied, and which act without any additional heat source. This means that the treatment can be carried out in a particularly simple way. The agents are simply introduced into the habitat of the insects.

The treatment ends by removing the agent. This prevents the parasites being exposed to constantly decreasing concentrations of active compound. This prevents resistance build-up in the parasites.

The long-term release of active compound of these agents permits long-term therapy which also protects the progeny from the insect nests.

In these agents, the active compound can be contained in, or incorporated into, carrier substances, or it can be applied to carrier substances in a suitable form.

Carrier substances are shaped articles which are attached at, or inside, the habitat of the insects. It is also possible that parts of the habitat are formed from material into which the active compound is incorporated, or onto whose surface the active compound is applied, or which is soaked or impregnated with active compound. For example, in the case of bees, partitions are preferred which are pushed in between the honeycombs and have been treated with agents containing the active compound or into which the active compound is incorporated.

Carrier substances can be natural or synthetic carrier substances. Examples of natural carrier substances are wood, wood processing products, cardboard, paper, gum, rubber, felt, metal, glass, porcelain or ceramic materials. Examples of synthetic carrier substances are plastics on a polyvinyl basis, PVC, polyacrylate, polymethacrylate, epoxide, polyurethane, polyester, polyamide, cellulose and its derivatives, polyethylene, polypropylene and synthetic rubber.

However, other suitable carrier substances are layers which are applied onto a solid or flexible base. Such layers can be absorptive and be treated with agents containing the active compound. But such layers can also be non-absorptive and contain the active compound in incorporated form. As a rule, these layers are polymers with good adhesive properties, to which inert filler substances may be added. Polymers which are employed for this purpose are the raw materials for varnish in the paint industry, as well as, for example, cellulose derivatives, acrylates and methacrylates.

Examples which may be mentioned of fillers for the preparation of absorptive layers are: kaolin, calcium carbonate, silicates, bentonites, cellulose, cellulose derivatives, starch and wood powder. Here, the active compound is either already incorporated in the layer-forming material, or the layer is, for example, soaked or impregnated or sprayed at a later point in time with the above described agent to be sprayed.

Layers which contain the active compound in an incorporated form can also be formed by paints or varnishes containing the active compound. These contain the active compound in a concentration of 0.00001-10, preferably 0.001-1, percent by weight, in addition to the customary basic coating composition. Dispersion paints and varnishes are preferably employed as basic coating composition.

Layers which contain the active compound in an incorporated form can, however, also be films, strips or tapes which have one or more layers, and which may be self-adhesive.

Thus, a self-adhesive film containing the active compound, can consist, for example, of an adhesive layer, a flexible carrier layer, a flexible carrier layer containing the active compound, and a flexible top layer without active compound. The individual layers consist of polymer materials which are known per se and which are suitable for the manufacture of such layers.

As already mentioned, these shaped articles can contain the active compound in an incorporated form. The shaped articles contain the active compound in concentrations of 0.00001-10% by weight, preferably 0.00001-1% by weight, relative to the basic material of the shaped article.

Suitable shaped articles are strips, tapes, plates, but also, as mentioned further above, component parts.

Substances which can be used for the manufacture of the shaped articles according to the invention are polyvinyl resins, polyacrylates, epoxy resins, cellulose, cellulose derivatives, polyamides and polyesters which are sufficiently compatible with the abovementioned active compounds. The polymers must be sufficiently firm and flexible in order not to tear or become friable during shaping. They must permit sufficient migration of the active compounds towards the surface of the shaped article.

Examples of typical vinyl resins are polyvinyl halides, such as polyvinyl chloride, polyvinyl chloride/vinyl acetate and polyvinyl fluoride; polyacrylate esters and polymethacrylate esters, such as polymethyl acrylate and polymethyl methacrylate; and polyvinyl benzenes, such as polystyrene and polyvinyltoluene.

Suitable plasticizers for the manufacture of the shaped articles on a polyvinyl resin basis, according to the invention, are those which are customarily used for plasticizing solid vinyl resins. The plasticizer used depends on the resin and its compatibility with the plasticizer. Examples of suitable plasticizers are esters of phosphoric acid, such as tricresyl phosphate, esters of phthalic acid, such as dimethyl phthalate and dioctyl phthalate, and esters of adipic acid, such as diisobutyl adipate. It is also possible to use other esters, such as the esters of azelaic acid, maleic acid, ricinoleic acid, myristic acid, palmitic acid, oleic acid, sebacic acid, stearic acid and trimellitic acid, as well as complex linear polyesters, polymer plasticizers and epoxidized soya bean oils. The amount of plasticizer is approximately 10 to 50% by weight, preferably about 20 to 45% by weight, of the entire composition.

The shaped articles can additionally contain further constituents, such as stabilizers, lubricants, fillers and colorants, without this altering the essential properties of the composition. Suitable stabilizers are antioxidants and agents which protect the shaped article from ultraviolet rays and undesirable degradation during processing, such as extruding. Some wetting agents, such as epoxidized soya bean oils, furthermore serve as secondary plasticizers. Lubricants which can be used are, for example, stearates, stearic acid and polyethylene having a low molecular weight. These constituents can be used in a concentration of up to about 20% by weight of the total composition.

During the manufacture of the shaped articles on a vinyl resin basis, according to the invention, the various constituents are mixed in the dry state by known mixing processes, and pressed into shape by known extruding or injection moulding processes.

The choice of the processing procedure for the manufacture of the shaped articles according to the invention depends, from the technical point of view, basically on the rheological properties of the material for the shaped articles and the shape of the desired body. The processing procedures can be regulated either by the processing technology or by the type of the shaping. In the process technology, the processes can be divided by virtue of the rheological states through which the pieces pass during the procedure. Accordingly, suitable procedures for viscous materials for shaped articles are casting, pressing, injecting and applying, and for elastoviscous polymers, injection molding, extruding, calendering, rolling and, where appropriate, edging. Divided into the types of shaping, the shaped articles according to the invention may be produced by casting, dipping, pressing, injection molding, extruding, calendering, stamping, bending, deep-drawing and the like.

These processing procedures are known and need no further explanation. In principle, the comments which have been made hereinbefore by way of example for polyvinyl resins are also true for polymers, such as polyamides and polyesters.

Agents which act by a systemic action via the haemolymph of the insects are, for example, feedstuffs containing the active compound. Feedstuffs which may be mentioned are: sugar granules, sugar-containing mixtures, solutions, suspensions or emulsions. These contain concentrations of active compound of 0.5–20% by weight, preferably of 1–10% by weight. These mixtures are diluted further to application concentrations of the active compound of $10^{-8}$–1% by weight, preferably 0.0001–0.01% by weight, particularly preferably to 0.0001–0.005% by weight, with water or sugar solution.

Ready-to-use feedstuff doughs or pastes which contain the active compound in the application concentration, in addition to sugar and starch, may furthermore be mentioned.

Agents for an application of the active compounds in the drinking water are particularly preferred. Suitable for this purpose are water-miscible solutions of the active compounds which contain one or more polar solvents and have an alkaline reaction.

To prepare such solutions, the active compound is dissolved in a polar, water-soluble solvent, which either has an alkaline reaction or to which an alkaline, water-soluble substance is added. The latter is expediently also dissolved in the solvent, but can also be suspended in the solvent and only dissolved in the drinking water. Here, the drinking water should have a pH of higher than 7 after the addition of the active compound solution, but preferably a pH of higher than 8 and lower than 11.

The drinking water can contain sugar (glucose) in an amount of 0.1 to 5% by weight, preferably of about 1% by weight.

The solution of the active compound concentrate should not exceed a pH of 11.

The concentration of the active compound can be in the range of 0.5 to 50%, but preferably in the range of 1 to 25%.

Suitable solvents are all water-soluble solvents in which the active compound is soluble in a sufficient concentration, and which are physiologically acceptable.

These solvents are, from the series of the alcohols, monohydric and polyhydric alcohols, such as, for example, ethyl alcohol, isopropyl alcohol, benzyl alcohol, glycerol, propylene glycol, polyethylene glycols, poly(oxyethylene)/poly(oxypropylene) polymers and basic alcohols, such as, for example, monoethanolamine, diethanolamine and triethanolamine.

Solvents which are additionally suitable are ketones, for example acetone or methyl ethyl ketone, and, from the series of the esters, for example ethyl lactate. Other solvents, such as N-methylpyrrolidone, dimethylacetamide or dimethylformamide, can likewise be employed.

Bases which are to be employed to establish the alkaline pH are preferably organic bases, for example basic amino acids, such as L- or D,L-arginine, L- or D,L-lysine, methylglucosamine, glucosamine, 2-amino-2-hydroxymethyl-propane-1,3-diol, choline, or piperazine. Diamines are also suitable for this purpose, for example N,N,N,′N′-tetrakis-(2-hydroxypropyl)-ethylene-diamine or polyether-tetrole on the basis of ethylenediamine (M.W. 480–420, OH index 432 ∝ 467) also forms clear solutions in the indicated pH range. It is also possible to employ inorganic bases, for example ammonia or sodium carbonate, if appropriate with the addition of water.

Substances which are usually used as emulsifiers or solubilizers and which are colloidally soluble in water, can be employed in this case like polar solvents if a basic auxiliary is additionally admixed to them.

To prepare the solutions, the substances are weighed into a container equipped with a stirrer, and then stirred with heating until a clear solution has formed.

Examples of preparations active compounds are:

EXAMPLE 1

2.5 g of active compound of Example 4 are dissolved in 100 ml of triethanolamine, with heating.

EXAMPLE 2

2.5 g of active compound of Example 4 and 12.5 g of lactic acid are dissolved in 100 ml of triethanolamine with heating and stirring.

EXAMPLE 3

10.0 g of active compound of Example 4 are dissolved in 100 ml of monoethanolamine.

| Example 4 | |
| --- | --- |
| Active compound of formula I | 5.0 g |
| Propylene glycol | 50.0 g |
| Sodium carbonate | 5.0 g |
| Water to | 100 ml |
| Example 5 | |
| Active compound of formula I | 5.0 g |
| Monoethanolamine | 10 g |
| N-Methylpyrrolidone to | 100 ml |
| Example 6 | |
| Active compound of formula I | 2.5 g |
| Sodium carbonate | 5.0 g |
| Polyethylene glycol 200 to | 100 ml |

The active compound is dissolved in the polyethylene glycol with heating, and sodium carbonate is suspended therein.

| Example 7 | | |
| --- | --- | --- |
| Active compound of Example 4 | | 20 g |
| Emulgator Toximul ® | (mixture of Ca alkylbenzenesulphonate and non-ionic emulsifiers and methanol, having a hydrophilic/lipophilic balance HLB value: 10) | 7 g |
| Emulgator Toximul S ® | (mixture of Ca alkylbenzenesulphonate and non-ionic emulsifier, methanol, having a hydrophilic/lipophilic balance HLB value: 10) | 5 g |
| Solvesso 200 ® | (alkylnaphthalene mixture of high-boiling mineral oil fractions) to | 100 ml |
| Example 8 | | |
| Active compound of Example 4 | | 16 g |
| Emulgator 368 ® | Alkylaryl polyglycol ether (molecular weight about 1165) | 9 g |
| Emulgator N P 10 ® | Nonylphenol polyglycol ether | 9 g |
| Dimethylformamide | | 10 g |
| Solvesso 200 to | | 100 ml |
| Example 9 | | |
| Active compound of Example 4 | | 5 g |

| -continued | | |
| --- | --- | --- |
| Emulgator Atlox ® | (mixture of polyoxyethylene ether, polyoxyglyceride and alkylarylsulphonate - readily water-soluble) | 4 g |
| Emulgator Atlox 3404 ® | (mixture of polyoxyethylene alkylaryl ether and alkylarylsulphonate - forms an emulsion in water) | 2 g |
| Emulgator Atlox 3409 ® | (mixture of non-ionic and anionic emulsifiers - soluble in water) | 4 g |
| Solvent PC 2 | (high-boiling aromatic mineral oil fraction) to Example 10 | 100 ml |
| Active compound of Example 4 | | 1 g |
| Dowanol DPM ® | (Dipropylene glycol methyl ether) to Example 11 | 100 ml |
| Active compound of Example 4 | | 0.5 g |
| Wetting agent: | Emulvin W ® (alkylaryl polyglycol ether) | 3.0 g |
| | Water to | 100 ml |

An example of a dusting agent is:

EXAMPLE 12

1 g of active compound of Example 4 is thoroughly mixed with 99 g of talc. From this mixture, 5 g are thoroughly mixed with 95 g of talc.

| Example of a PVC shaped article: Example 13 | |
| --- | --- |
| Active compound of Example 4 | 0.5 g |
| Isobutyl adipate | 15.5 g |
| Dialkyl pythalate | 8.0 g |
| Polyoxyethylated castor oil | 2.0 g |
| Stearic acid | 0.8 g |
| Colorant | 0.1 g |
| Polyvinyl chloride | 73.1 g |
| | 100.0 g |

100.0 kg of this mixture are mixed in a mixer until homogeneous, following the customary procedure for soft PVC.

This mixture is processed on an injection molding machine to give a honeycomb partition. Partition weight: 86.0 g.

The above mixture is prepared using 0.25 in place of 0.5 g of active compound and rolled on a suitable calendering device to give a film of the size of a DIN A4 sheet. Weight of the film: 50.0 g. The sheet is inserted for example in the beehive.

Example of a coated carrier:

EXAMPLE 14

A solution of active compound of Example 4 in Emulgator Span 20/Atlas and ethanol is uniformly distributed on a polyethylene film of thickness 2 mm, using a blade. The solution is adjusted so that 1 mg of active compound is applied per 100 $cm^2$ of surface area and 0.5 mg of emulsifier per 100 $cm^2$. The solvent is removed by evaporating, and the film is punched to give any desired shape.

Examples of a soaked carrier with the addition of polymer (=varnish):

EXAMPLE 15

Aluminum foils coated with kieselguhr are treated with a solution of active compound of Example 4 and polyvinyl alcohol in such a way that after drying 5 mg of active compound and 20 mg of polyvinyl alcohol remain per 100 cm² of film.

The carrier forms of the last two examples can be provided with an adhesive. After the adhesive protection has been removed, they can simply be stuck into the habitats of insects.

Examples of granules for feeding:

EXAMPLE 16

0.5 kg of active compound of Example 4 are dissolved in 7.5 l of ethanol with careful heating and poured onto 99.5 kg of sugar contained in a granulating mixer while the mixer is running. The sugar, which is wet with alcohol and impregnated uniformly, is dried and, if required, sifted. Before use, 1.0 g of the granules are dissolved in 100 ml of water to give a sugar solution on which the insects feed.

EXAMPLE A 10 adult honey bees (*Apis mellifera*) which were infected with *Nosema apis* were kept for 48 hours at 25° C. and treated via the feed with saturated, aqueous sucrose solution which contained 10 ppm of active compound of Example 4.

At the end of the experiment, all 10 animals were alive and were then destroyed. Analysis by transmission electron microscopy detected cytolysis of the merogonic and sporogonic stages of *Nosema apis*.

In a control group which had only been fed saturated sugar solution, 4 out of 10 animals died. The survivors were heavily infected with all stages of *Nosema apis*, as was found with reference to analyses by optical microscopy and transmission electron microscopy.

Examples of active compounds:

EXAMPLE 1

2-[4[(4'Chloro)-2'-thiazolyloxy]phenyl]-3,5(2H,4H)-dioxo-1,2,4-triazine

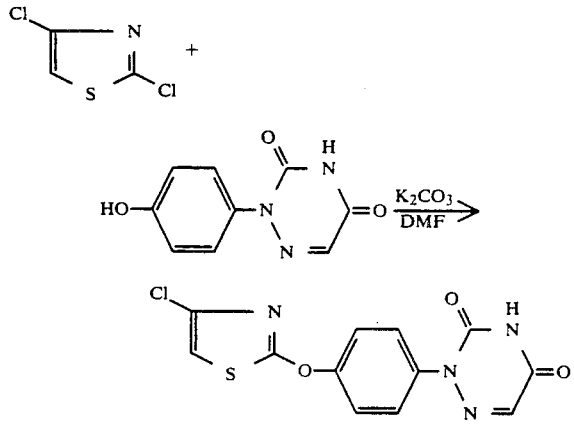

29 (0.01 mol) of hydroxyphenylazauracil, 1.5 g (0.01 mol) of dichlorothiazole and 1.4 g (0.01 mol) of potassium carbonate are refluxed for 2 hours in 20 ml of dry DMF, with stirring. When the reaction mixture has cooled down, it is acidified using HCl, and any product that has precipitated is filtered off with suction. After recrystallization from ethanol, 2.9 g (90% of theory) of thiazolyloxyarylazauracil are obtained.

The following are prepared analogously:

EXAMPLE 2

2-[4-[4'-Chloro-5'-methyl)-2'-thiazolyloxy]-phenyl]1,2,4-triazine-3,5(2H,4H)-dione.

EXAMPLE 3

2-(4-(2'-Benzothiazolyloxy)-phenyl)-1,2,4-triazine-3,5(2H,4H)dione.

EXAMPLE 4

2-[4[6'-Chloro)2'-benzothiazolyloxy]-3,5-dichlorophenyl]1,2,4-triazine-3,5-(2H,4H)dione.

EXAMPLE 5

2-[4-[(4'-Chloro)-2'-thiazolyloxy]phenyl]- 4-N-methyl-3,5-(2H,4H)-dioxo-1,2,4-triazine

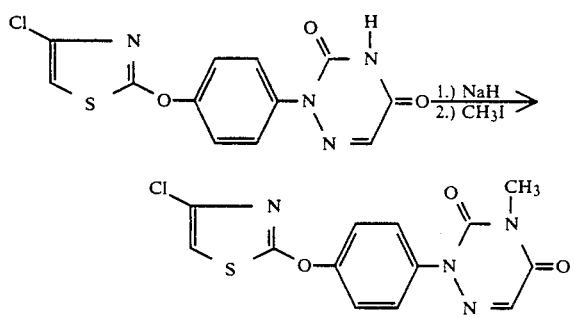

2 g (6 mmol) of thiazolyloxyarylazauracil are dissolved in 20 ml of absolute DMSO, and 0.14 g (6 mmol) of sodium hydride are added. The mixture is stirred for 20 minutes at room temperature, and 1.3 g (9 mmol) of methyl iodide in 5 ml of DMSO are then added under argon. The mixture is warmed to 50° C. and kept at this temperature for 3 hours.

The reaction mixture is subsequently concentrated in vacuo, and water is then added. After the solid which has precipitated is filtered off with suction, 1.5 g (71% of theory) of the N-methyl compound are obtained in this manner.

EXAMPLE 6

2-[4-[6'-Chloro)2'-benzoxazolylsulphoxyl]-3,5-dichlorophenyl]1,2,4-triazine-3,5(2H,4H)dione

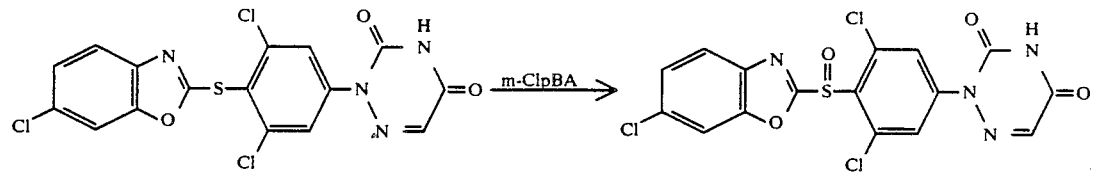

10 g (0.027 mol) of chlorobenzoxazolylthiophenylazauracil are dissolved in a mixture of 200 ml of methanol and 100 ml of dichloromethane. The mixture is cooled to 10° C., 4.6 g or m-chloroperbenzoic acid m-ClpBA (85% strength) are added at this temperature. Stirring is continued for 10 hours, and the solvent is then stripped off in vacuo at 10° C. and the residue is recrystallized from isopropanol. 8.5 g (82% of theory) of sulphoxide are obtained in this manner.

EXAMPLE 7

2-[4-(2'-Benzoxazolylsulphoxyl)-phenyl]1,2,4-triazine-3,5(2H,4H)dione.

EXAMPLE 8

2-[4-[(6'-Chloro)-2'-benzoxazolylsulphonyl]-3,5-dichlorophenyl]1,2,4-triazine-3,5(2H,4H)dione

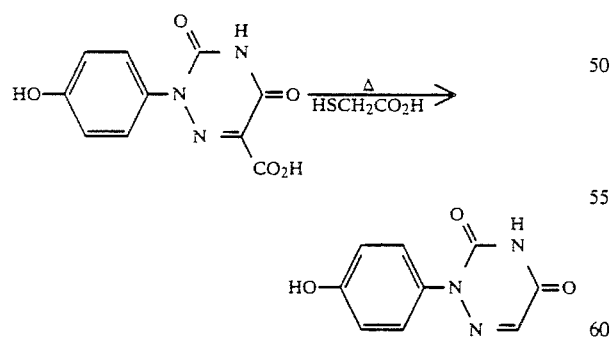

8.8 g (0.02 mol) of chlorobenzoxazolylthiophenylazauracil are dissolved in 100 ml of glacial acetic acid and the mixture is stirred under reflux for 18 hours with 40 ml of 30% strength hydrogen peroxide. After the mixture has cooled down, water is added, and the solid which has precipitated is filtered off with suction. Recrystallization from isopropanol yields 6.9 g of sulphone (73% of theory).

EXAMPLE 9

2-[4-(2'-Benzoxazolylsulphonyl)-3,5-dichlorophenyl]1,2,4-triazine-3,5(2H,4H)dione.

EXAMPLE 10

2-[4-(2'-Benzoxazolylsulphony-1)-phenyl]1,2,4-triazine-3,5(2H,4H)dione.

Example of the preparation of starting compounds of the formula II:

2-(4-Hydroxyphenyl)-1,2,4-triazine-3,5(2,4H)dione

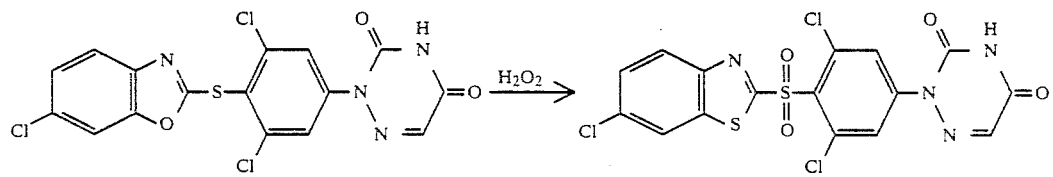

34 g (0.137 mol) of carboxylic acid in 34 ml of mercaptoacetic acid are heated at 170° C. After 1.5 hours, the mixture is allowed to cool, water is added, and 24 g (82% of theory) of the decarboxylated product are obtained after filtration.

Example of the preparation of the starting compounds of formula V:

2-(4-Hydroxyphenyl)-3,5(2H,4H)dioxo-1,2,4-triazine-6-carboxylic acid

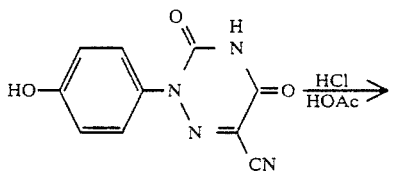

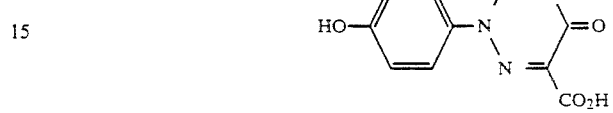

30.1 g (0.13 mol) of cyanoazauracil in 1000 ml of HCl/glacial acetic acid (1:1) are stirred under reflux for 14 hours. After the mixture has cooled down, it is evaporated, water is added to the residue, and any product which has precipitated is filtered off with suction 19 g (59% of theory)

Example of the preparation of the starting compounds of the formula VI:

2-(4-Hydroxyphenyl)-3,5-(2H,4H),dioxo-6-cyano-1,2,4-triazine

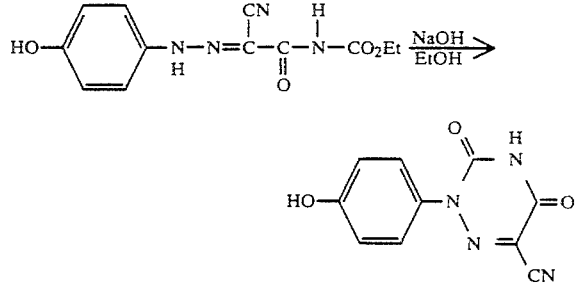

43.8 g (0.158 mol) of the hydrazonocyanourethane and 8.5 g (0.213 mol) of NaOH in 400 ml of absolute ethanol are refluxed for 2 hours. The mixture is subsequently cooled, acidified using hydrochloric acid and concentrated in vacuo. The concentrate is stirred with water, and the solid which has precipitated is filtered off with suction. 30.1 g (85% of theory) of cyanoazauracil are obtained in this manner after drying. Example of the preparation of the starting compounds of the formula VII Ethyl N-[[[cyano(4-hydroxyphenyl)-hydrazinylidene]methyl]carbonyl]-crabamate

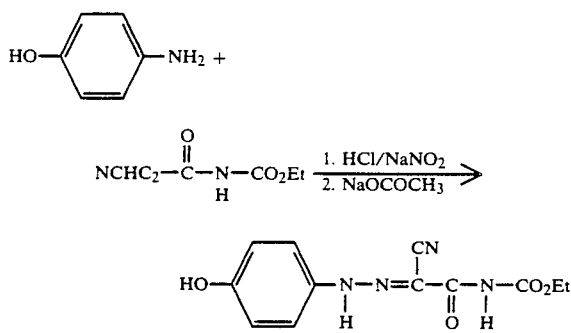

10 g (0.091 mol) of 4-hydroxyaniline are dissolved in 19.7 ml of concentrated HCl and 200 ml of glacial acetic acid, and a solution of 6.4 g (0.092 mol) of sodium nitrite in 30 ml of water is added dropwise at 0°-5° C. Stirring is continued until a clear solution has formed, a mixture of 14.3 g (0.092 mol) of cyanoacetylurethane and 21 g (0.25 mol) of sodium acetate is then added, and stirring is continued for 3 hours at 10° C. The reaction mixture is concentrated in vacuo, the concentrate is stirred with water and the solid is filtered off with suction. In this manner, 19 g (75%) of product are obtained as a finely-crystalline yellow powder.

What is claimed is:

1. A method of combating Protozoa in insects comprising treating said insects of their habitat with an effective amount to combat Protozoa in insects of at least one substituted 1,2,4-triazinedione of the formula

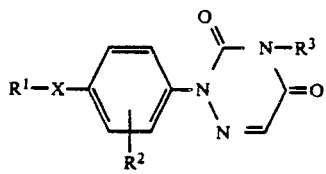

in which
R$^1$ represents unsubstituted or substituted aromatic radical or an unsubstituted or substituted heteroaromatic radical which is bonded via carbon,
X represents O, S, SO, SO$_2$, or

R$^2$ represents one or more identical or different radicals said radical being hydrogen, halogen, nitro, alkyl, alkoxy, halogenoalkyl or halogenoalkoxy,
R$^3$ represents hydrogen or unsubstituted or substituted alkyl, alkenyl, alkinyl or aralkyl, and salts of said triazinedione with bases.

2. A method according to claim 1,
in which
X represents O or

R$^1$ represents thiazolyl, benzothiazolyl, benzoxazolyl or phenyl, each of which is unsubstituted or substituted by C$_{1-4}$-alkyl, C$_{1-4}$-halogenoalkyl, halogen, nitro, CN, or C$_{1-4}$-alkoxy, C$_{1-4}$-halogenoalkoxy, C$_{1-4}$-alkylthio, or C$_{1-4}$-halogenoalkylthio,
R$^2$ represents one or more radicals said radicals being hydrogen, halogen, or C$_{1-4}$-alkyl, and
R$^3$ represents hydrogen 3. A method according to claim 1,
in which
X represents O,
R$^1$ represents thiazolyl or benzothiazolyl, each of which is unsubstituted or substituted by chlorine, methyl or trifluoromethyl,
R$^2$ represents one or more radicals said radicals being hydrogen, methyl or chlorine,
R$^3$ represents hydrogen.

4. A method according to claim 1,
in which
X represents

R$^1$ represents phenyl which is unsubstituted or substituted by chlorine, methyl or trifluoromethyl,
R$^2$ represents one or more identical or different radicals said radicals being hydrogen, chlorine or methyl,
R$^3$ represents hydrogen or methyl.

5. A method according to claim 1, wherein said triazinediones are selected from the group consisting of 2-chloro-α-(4-chlorophenyl)-4-(4,5-dihydro-3,5-dioxo-1,2,4-triazin-2(3 H)-yl)-phenylacetonitrile and 2,6-dichloro-o-(4-chlorophenyl)-4-(4,5-dihydro-3,5-dioxo-1,2,4-triazin-2(3H)-yl)-phenylacetonitrile.

6. A method according to claim 1, wherein said insects are treated by direct contact or by systemic action.

7. An antiprotozoal composition useful for combating protozoa in insects comprising a 1,2,4-triazinedione of the formula

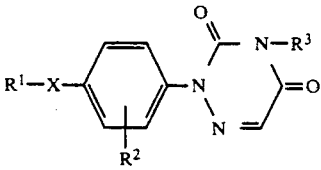

in which
R$^1$ represents an unsubstituted or substituted aromatic radical or an unsubstituted or substituted heteroaromatic radical which is bonded via carbon,
X represents O, S, SO, SO$_2$ or

R$^2$ represents one or more identical or different radicals said radicals being hydrogen, halogen, nitro, alkyl, alkoxy, halogenoalkyl or halogenoalkoxy,
R$^3$ represents hydrogen or an unsubstituted or substituted alkyl, alkenyl, alkinyl or aralkyl as well as salts thereof with bases and a carrier that is tolerated by insects.

* * * * *